United States Patent [19]

Pastor et al.

[11] Patent Number: 5,629,426
[45] Date of Patent: May 13, 1997

[54] CARBONATE-MEDIATED HYDROGEN PEROXIDE OXIDATIONS OF 4-HYDROXY-2,2,6,6-TETRAMETHYLPIPERIDINE

[75] Inventors: Stephen D. Pastor, Danbury, Conn.; Andrea R. Smith, Wingdale, N.Y.; Kurt M. Bessonen, Mobile, Ala.

[73] Assignee: Ciba-Geigy Corporation, Tarrytown, N.Y.

[21] Appl. No.: 555,823

[22] Filed: Nov. 9, 1995

[51] Int. Cl.$^6$ .................................................. C07D 211/46
[52] U.S. Cl. .................................................. 546/216
[58] Field of Search ............................. 546/216

[56] References Cited

U.S. PATENT DOCUMENTS

| | | | |
|---|---|---|---|
| 4,665,185 | 5/1987 | Winter et al. | 546/184 |
| 5,254,760 | 10/1993 | Winter et al. | 585/5 |
| 5,416,215 | 5/1995 | Rüschken et al. | 546/184 |

OTHER PUBLICATIONS

J. Keana, Chemical Reviews, vol. 78 No. 1 (1978) pp. 38–64.

M. Dagonneau et al., Synthesis, Nov. 1984 pp. 895–916.

E. Rozantsev et al., Synthesis, Aug. 1971, pp. 401–414.

E. Rozantsev et al. Synthesis, Apr. 1971, pp. 190–202.

G. Sosnovsky et al., Z. Naturfor–Ch. 31b. pp. 1376–1378 (1976).

J. Zakrzewski, Journal f. Prakt. Chemie Band, 327, Heft 6, 1985 S. 1011–1014.

M. E. Brik, Tetrahedron Letters, vol. 36 No. 31 pp. 5519–5522 (1995).

E. Rauckman et al. Synthetic Comm. 5(6) 409–413 (1975).

Levina, T.M. et al, Dokl. Akad. Nauk. SSSR, 1981, 261(1), pp. 109–110.

*Primary Examiner*—C. Warren Ivy
*Assistant Examiner*—Garth M. Dahlen
*Attorney, Agent, or Firm*—Luther A. R. Hall

[57] ABSTRACT

An environmentally friendly process is described for the preparation of 4-hydroxy-2,2,6,6-tetramethylpiperidine-N-oxyl by the carbonate-mediated hydrogen peroxide oxidation of 4-hydroxy-2,2,6,6-tetramethylpiperidine.

11 Claims, No Drawings

CARBONATE-MEDIATED HYDROGEN PEROXIDE OXIDATIONS OF 4-HYDROXY-2,2,6,6-TETRAMETHYLPIPERIDINE

The instant invention pertains to the hydrogen peroxide oxidation of 4-hydroxy-2,2,6,6-tetramethylpiperidine to the corresponding 4-hydroxy-2,2,6,6-tetramethylpiperidine-N-oxyl compound using hydrogen peroxide and an ammonium or alkali metal carbonate or bicarbonate catalyst.

BACKGROUND OF THE INVENTION 2,2,6,6-Tetramethylpiperidine and its derivatives are important spin traps for labelling biological molecules. This is illustrated in a number of reviews as follows: J. F. W. Keana, Chemical Reviews, 78, 37 (1978); M. Dagonneau et al., Synthesis, 1984, 895; E. G. Rozantsev et al., Synthesis 1971, 401; and E. G. Rozantsev et al., Synthesis, 1971, 190.

Such compounds are also disclosed as inhibitors for preventing the premature polymerization of vinyl monomers as seen in U.S. Pat. No. 5,254,760.

The oxidation of 4-substituted 2,2,6,6-tetramethylpiperidine to the corresponding N-oxyl derivatives is known to occur by a number of different processes. U.S. Pat. No. 4,665,185 describes using tert-butyl hydroperoxide with transition metal catalysts. G. Sosnovsky et al., Z. Naturforsch. 31b, 1376 (1976); J. Zakrzewski, J. Prakt. Chem., 327, 1011 (1985) and E. G. Rozantsev et al., Synthesis, 1971, 190 each teach the use of hydrogen peroxide with sodium tungstate catalyst. U.S. Pat. No. 5,416,215 teaches the use of hydrogen and selected divalent metal salts. M. E. Brik, Tetrahedron Letters, 36, 5519 (1995) teaches the oxidation of secondary amines to nitroxides using Oxone® (potassium peroxomonosulfate) in aqueous buffered solutions.

E. J. Rauckman et al., Syn. Communications 5(6), 409 (1975) describe inter alia the oxidation of secondary amines to nitroxides using catalytic amounts of sodium tungstate in the presence of acetonitrile, methanol, hydrogen peroxide and sodium bicarbonate at room temperature for two days to give the oxyl compound in a yield of 85%. The required presence of the known sodium tungstate catalyst clearly differentiates the Rauckman process from the instant process where no sodium tungstate is present.

J. Zakrzewski, J. prakt. Chem., 327(6), 1011 (1985) does teach that 30% hydrogen peroxide in the presence of sodium carbonate gives the oxyl compound in a yield of 73%. The Zakrzewski reaction is run at room temperature (there is an exotherm requiring system cooling) and uses a large (three molar) excess of sodium carbonate for a two-day period. This large excess of sodium carbonate is clearly not a catalytic amount.

The instant process differs from that the Zakrzewski process by using only catalytic amounts of carbonate or bicarbonate rather than the large molar excess amount used by Zakrzewski; by running the reaction at elevated tempreatures rather than at room temperature; and by achieving very high yields and conversions of product (up to 99%) in a relatively short period of time (hours) rather than the two days needed for the Zakrzewski process.

It is clear that the instant process involves the use of an environmentally safe and friendly catalyst and avoids the presence of transition metals in waste waters. Sodium bicarbonate and sodium carbonate are easily handled, are economically inexpensive and cause no adverse environmental conditions. The instant process also gives the desired N-oxyl compounds in high yields and conversions without the use for costly and environmetally hazardous transition metals or divalent metal ions.

In a copending application Ser. No. 08/555,822 a process for the preparation of the N-oxyl compound by the oxidation of the corresponding secondary amine using hydrogen peroxide without any catalyst is described.

DETAILED DISCLOSURE

The instant invention pertains to an environmentally friendly process for the preparation of 4-hydroxy-2,2,6,6-tetramethylpiperidine-N-oxyl which comprises oxidizing 4-hydroxy-2,2,6,6-tetramethylpiperidine with an aqueous hydrogen peroxide solution in the presence of an effective catalytic amount of an ammonium or alkali metal carbonate or bicarbonate at a temperature of 60°–99° C.

Preferably the aqueous hydrogen peroxide is 30–50% by weight hydrogen peroxide; most preferably 50% by weight hydrogen peroxide.

While any of the alkali metal salts may be used including cesium and rubidium, preferably the alkali metal is sodium, potassium or lithium, most preferably sodium.

Specific catalysts found useful in the instant process are sodium carbonate, lithium carbonate, sodium bicarbonate, potassium carbonate, cesium carbonate and ammonium carbonate.

The effective amount of catalyst is from 0.05 to 0.3 mole % of catalyst based on the starting 4-hydroxy-2,2,6,6-tetramethylpiperidine.

Preferably the temperature range for the process is 85°–95° C.

A preferred embodiment of the process involves adding the hydrogen peroxide continuously over a 2–4 hour period to the reaction mixture.

The instant process may optionally have a metal passivator or chelator present. The EDTA type chelators such as ethylenediaminetetraacetic acid disodium salt are particularly suited since they remove trace amounts of iron or other metals encountered during manufacturing processes without interfering with the catalyst system. Iron or other metals may decompose the hydrogen peroxide unless removed by such a chelator.

The course of the reaction is monitored by GLC to determine the conversion of the N-H to N-oxyl compound. In theory 1.5 equivalents of hydrogen peroxide are needed to oxidize one equivalent of the starting material to the corresponding N-oxyl compound.

Any excess hydrogen peroxide may be destroyed using catalytic quantifies of platinum or palladium on charcoal.

Alternatively, any excess hydrogen peroxide may be destroyed facilely by the addition of sodium sulfite at an elevated pH (using sodium hydroxide) followed by the addition of acid for neutralization.

The N-oxyl compound may be isolated by using rotary evaporation of the water solvent under vacuum or other conventional means.

The oxidation of the starting material to the corresponding N-oxyl using hydrogen peroxide proceeds without a catalyst, but is perceptibly slower than the instant process. The advantages of the instant process, besides the clear environmental benefits, are a slightly better conversion with time and a quicker initiation of the oxidation reaction. The initiation of the reaction without catalyst is variable, leading to different levels of hydrogen peroxide built up in the reaction mixture. This can result in a strong exotherm at the initiation of the reaction which may cause difficulty in any scaled-up reaction. This is overcome by use of the instant catalyst which leads to a quicker onset of reaction, a somewhat higher conversion and a more reproducible and convenient process.

The following examples are for illustrative purposes only and are not to be construed to limit the scope of the instant invention in any manner whatsoever.

EXAMPLE 1

4-Hydroxy-2,2,6,6-tetramethylpiperidine-N-oxyl

To a solution of 100 g (0.636 mol) of 4-hydroxy-2,2,6,6-tetramethylpiperidine, 0.29 g of ethylenediaminetetraacetic acid disodium salt dihydrate and 0.14 g (1.3 mmol) of anhydrous sodium carbonate in 80 g of deionized water at 60° C. is added over a four-hour period using a syringe pump 130 g (1.91 mol) of 50% hydrogen peroxide. The reaction mixture is stirred for 18 hours. The conversion to 4-hydroxy-2,2,6,6-tetramethyl-piperidine-N-oxyl is 99.2% as determined by GLC analysis.

EXAMPLE 2

4-Hydroxy-2,2,6,6-tetramethylpiperidine-N-oxyl

A solution of 126.17 g (0.80 mol) of 4-hydroxy-2,2,6,6-tetramethylpiperidine, 0.74 g of ethylenediaminetetraacetic acid disodium salt dihydrate and 0.09 g (1.0 mmol) of anhydrous sodium bicarbonate in 100 mL of distilled water is heated to 70° C. To the resultant mixture is added over a two-hour period using a syringe pump 160 mL (2.61 mol) of 50% hydrogen peroxide. The temperature of the reaction mixture is raised to 95°–98° C. over the first 25 minutes of the addition of the hydrogen peroxide and then the reaction mixture is maintained at that temperature. Upon completion of the slow addition of the hydrogen peroxide, the conversion to 4-hydroxy-2,2,6,6-tetramethylpiperidine-N-oxyl is 99.1% as determined by GLC analysis.

EXAMPLE 3

4-Hydroxy-2,2,6,6-tetramethylpiperidine-N-oxyl

A solution of 126.91 g (0.81 mol) of 4-hydroxy-2,2,6,6-tetramethylpiperidine, 0.72 g of ethylenediaminetetraacetic acid disodium salt dihydrate and 0.09 g (1.0 mmol) of lithium carbonate in 100 mL of distilled water is heated to 70° C. To the resultant mixture is added over a two-hour period using a syringe pump 240 mL (2.35 mol) of 30% hydrogen peroxide. The temperature of the reaction mixture is raised to 90°–94° C. over the first 25 minutes of the addition of the hydrogen peroxide and then the reaction mixture is maintained at that temperature. Upon completion of the slow addition of the hydrogen peroxide, the conversion to 4-hydroxy-2,2,6,6-tetramethylpiperidine-N-oxyl is 91.2% as determined by GLC analysis.

EXAMPLE 4

4-Hydroxy-2,2,6,6-tetramethylpiperidine-N-oxyl

A solution of 126.17 g (0.80 mol) of 4-hydroxy-2,2,6,6-tetramethylpiperidine, 0.77 g of ethylenediaminetetraacetic acid disodium salt dihydrate and 0.12 g (1.0 mmol) of anhydrous sodium carbonate in 100 mL of distilled water is heated to 70° C. To the resultant mixture is added over a two-hour period using a syringe pump 240 mL (3.92 tool) of 50% hydrogen peroxide. The temperature of the reaction mixture is raised to 95°–98° C. over the first 25 minutes of the addition of the hydrogen peroxide and then the reaction mixture is maintained at that temperature. Upon completion of the slow addition of the hydrogen peroxide, the conversion to 4-hydroxy-2,2,6,6-tetramethylpiperidine-N-oxyl is 98.8% as determined by GLC analysis.

EXAMPLE 5

4-Hydroxy-2,2,6,6-tetramethylpiperidine-N-oxyl

A solution of 126.17 g (0.80 mol) of 4-hydroxy-2,2,6,6-tetramethylpiperidine, 0.77 g of ethylenediaminetetraacetic acid disodium salt dihydrate and 0.12 g (1.0 mmol) of anhydrous sodium carbonate in 100 mL of distilled water is heated to 75° C. To the resultant mixture is added over a five-hour period using a syringe pump 480 mL (4.70 mol) of 30% hydrogen peroxide. The temperature of the reaction mixture is raised to 91° C. over the first 25 minutes of the addition of the hydrogen peroxide and then the reaction mixture is maintained at 85°–90° C. Upon completion of the slow addition of the hydrogen peroxide, the conversion to 4-hydroxy-2,2,6,6-tetramethylpiperidine-N-oxyl is 98.9% as determined by GLC analysis.

EXAMPLE 6

4-Hydroxy-2,2,6,6-tetramethylpiperidine-N-oxyl

A solution of 126.75 g (0.81 mol) of 4-hydroxy-2,2,6,6-tetramethylpiperidine, 0.73 g of ethylenediaminetetraacetic acid disodium salt dihydrate and 0.12 g (1.0 mmol) of anhydrous sodium carbonate in 100 mL of distilled water is heated to 68° C. To the resultant mixture is added over a six-hour period using a syringe pump 480 mL (4.70 mol) of 30% hydrogen peroxide. The temperature of the reaction mixture is raised to 80° C. over the first 20 minutes of the addition of the hydrogen peroxide and then the reaction mixture is maintained at 80° C. Upon completion of the slow addition of the hydrogen peroxide, the conversion to 4-hydroxy-2,2,6,6-tetramethylpiperidine-N-oxyl is 90.8% as determined by GLC analysis.

The results of these Examples are summarized in the table below.

| Example | Reaction Temp. °C. | Conc % $H_2O_2$ | Percent Conversion | Catalyst |
| --- | --- | --- | --- | --- |
| 1 | 60 | 50 | 99.2 | $Na_2CO_3$ |
| 2 | 95–98 | 50 | 99.1 | $NaHCO_3$ |
| 3 | 95–98 | 30 | 91.2 | $Li_2CO_3$ |
| 4 | 95–98 | 50 | 98.8 | $Na_2CO_3$ |
| 5 | 85–90 | 30 | 98.9 | $Na_2CO_3$ |
| 6 | 80 | 30 | 90.8 | $Na_2CO_3$ |

EXAMPLE 7

4-Hydroxy-2,2,6,6-tetramethylpiperidine-N-oxyl

When the procedure of Example 1 is repeated using 1.5 equivalents of 50% aqueous hydrogen peroxide at 80° C, the conversion to the desired N-oxyl product after seven hours is 97.1% as determined by GLC.

EXAMPLE 8

4-Hydroxy-2,2,6,6-tetramethylpiperidine-N-oxyl

When the procedure of Example 1 is repeated using 2 equivalents of 50% hydrogen peroxide at 80° C. without any EDTA disodium salt passivator or chelator present, the conversion to the desired N-oxyl product after seven hours is 99.4%.

EXAMPLE 9

4-Hydroxy-2,2,6,6-tetramethylpiperidine-N-oxyl

When the sodium carbonate catalyst used in Example 4 is replaced with an equivalent amount of potassium carbonate, the N-oxyl compound is obtained in a conversion of 99.8% as determined by GLC analysis.

EXAMPLE 10

4-Hydroxy-2,2,6,6-tramethylpiperidine-N-oxyl

To a solution of 126.34 g (0.80 tool) of 4-hydroxy-2,2,6,6-tetramethylpiperidine, 0.75 g of ethylenediaminetetraacetic acid disodium salt dihydrate (0.002 mol) and 0.10 g (1.0 mmol) of ammonium carbonate in 100 g of deionized water at 70° C. is added over a four-hour period using a syringe pump 160 g (2.61 tool) of 50% hydrogen peroxide. The temperature initially rises to 94° C., but then fails to 87° C. The reaction mixture is stirred overnight at a temperature of 78°–87° C. The conversion to 4-hydroxy-2,2,6,6-tetramethyl-piperidine-N-oxyl is 99.8% as determined by GLC analysis.

EXAMPLE 11

4-Hydroxy-2,2,6,6-tetramethylpiperidine-N-oxyl

When the sodium carbonate catalyst used in Example 4 is replaced with an equivalent amount of cesium carbonate, the N-oxyl title compound is obtained in a conversion of 99.5% as determined by GLC analysis.

EXAMPLE 12

4-Hydroxy-2,2,6,6-tetramethylpiperidine-N-oxyl

When the sodium carbonate catalyst used in Example 1 is replaced with an equivalent amount of ammonium bicarbonate, the N-oxyl title compound is obtained in excellent conversion.

EXAMPLE 13

4-Hydroxy-2,2,6,6-tetramethylpiperidine-N-oxyl

To a solution of 126.0 g (0.80 tool) of 4-hydroxy-2,2,6,6-tetramethylpiperidine, 0.37 g of ethylenediaminetetraacetic acid disodium salt dihydrate (0.001 mol) and 0.18 g (1.7 retool) of sodium carbonate in 100 g of deionized water at 80° C. is added over a three-hour period 110 g (1.62 tool) of 50% hydrogen peroxide. The reaction mixture is held at 80° C. for four hours. The residual hydrogen peroxide is reduced by adding 40 g (0.317 tool) of solid sodium sulfite at 70° C. and adjusting the pH to about 12 using 50% aqueous sodium hydroxide solution. The product is isolated after neutralization of the mixture with acetic acid and sodium sulfate solution. The yield of 4-hydroxy-2,2,6,6-tetramethylpiperidine-N-oxyl is 96%.

It is clear that the instant process gives the desired N-oxyl compound in excellent conversion in the presence of an ammonium or alkali metal carbonate or bicarbonate catalyst using hydrogen peroxide. This process affords the desired N-oxyl end product without the concomitant undesired heavy metal catalyst waste products which are environmentally hazardous. The by-products of the instant process such as water and the use of simple ammonium or alkali metal carbonate or bicarbonate catalysts do not present any severe pollution problems in waste water streams.

What is claimed is:

1. An environmentally friendly process for the preparation of 4-hydroxy-2,2,6,6-tetramethylpiperidine-N-oxyl which comprises oxidizing 4-hydroxy-2,2,6,6tetramethylpiperidine with an aqueous hydrogen peroxide solution in the presence of an effective catalytic amount of an ammonium or alkali metal carbonate or bicarbonate at a temperature range of 60°–99° C. and in the presence of a metal passivator.

2. A process according to claim 1 wherein the alkali metal is sodium, potassium or lithium.

3. A process according to claim 2 wherein the alkali metal is sodium.

4. A process according to claim 1 wherein the catalyst is sodium carbonate, lithium carbonate, sodium bicarbonate, potassium carbonate, cesium carbonate or ammonium carbonate.

5. A process according to claim 1 wherein the effective amount of catalyst is from 0.05 to 0.3 mole % of catalyst based on the starting 4-hydroxy-2,2,6,6-tetramethylpiperidine.

6. A process according to claim 1 wherein the temperature range for the process is 85°–95° C.

7. A process according to claim 1 wherein the aqueous hydrogen peroxide is 30–50% by weight hydrogen peroxide.

8. A process according to claim 7 wherein the aqueous hydrogen peroxide is 50% by weight hydrogen peroxide.

9. A process according to claim 1 wherein the hydrogen peroxide is added continuously over a 2 to 4 hour-period to the reaction mixture.

10. A process according to claim 1 wherein the metal passivator is ethylenediaminetetraacetic acid disodium salt.

11. A process according to claim 1 wherein the amount of aqueous hydrogen peroxide is from 1.5 to 2 equivalents per equivalent of 4-hydroxy-2,2,6,6-tetramethylpiperidine.

* * * * *